United States Patent

Belliotti et al.

[11] Patent Number: 5,977,110
[45] Date of Patent: Nov. 2, 1999

[54] SUBSTITUTED CYCLOHEXYLAMINES AS CENTRAL NERVOUS SYSTEMS AGENTS

[75] Inventors: Thomas R. Belliotti, Saline; Suzanne R. Kesten, Ann Arbor; Thomas A. Pugsley, Ann Arbor; David J. Wustrow, Ann Arbor, all of Mich.

[73] Assignee: Warner-Lambert Company, Morris Plains, N.J.

[21] Appl. No.: 09/043,331

[22] PCT Filed: Aug. 23, 1996

[86] PCT No.: PCT/US96/13687

§ 371 Date: Mar. 20, 1998

§ 102(e) Date: Mar. 20, 1998

[87] PCT Pub. No.: WO97/11070

PCT Pub. Date: Mar. 27, 1997

Related U.S. Application Data

[60] Provisional application No. 60/004,193, Sep. 22, 1995.

[51] Int. Cl.$^6$ ............ A61K 31/505; A61K 31/495; C07D 403/02; C07D 403/12; C07D 403/14; C07D 417/02; C07D 417/12; C07D 417/14

[52] U.S. Cl. ............ 514/252; 544/360; 544/295; 544/292; 544/293; 544/357; 544/369; 544/368; 544/370; 544/296; 544/284; 544/364; 544/405; 544/336; 546/264; 546/270.7; 546/270.1; 546/273.4; 546/270.4; 546/194; 546/209; 546/198; 546/199; 546/256; 546/257; 514/253; 514/254; 514/332; 514/256; 514/275; 514/260; 514/342; 514/338; 514/318; 514/326; 514/321; 514/322; 514/333; 544/328; 544/331

[58] Field of Search ............ 544/295, 296, 544/284, 360, 364, 369, 368, 357, 370; 514/252, 253, 254

[56] References Cited

U.S. PATENT DOCUMENTS 5,047,406 9/1991 Caprathe et al. ............ 514/252
5,478,828 12/1995 Mattson et al. ............ 514/253

FOREIGN PATENT DOCUMENTS 0431580 6/1991 European Pat. Off. .

OTHER PUBLICATIONS

Wustrow et al., "Aminopyrimidines with High Affinity for Both Serotonin and Dopamine Receptors," J. Med. Chem., vol. 41, No. 5, pp. 760–771, 1998.

*Primary Examiner*—Mukund J. Shah
*Assistant Examiner*—Ann M. Kessinger
*Attorney, Agent, or Firm*—Francis J. Tinney

[57] ABSTRACT

Substituted cyclohexylamines and derivatives thereof are described, as well as methods for the preparation and pharmaceutical composition of same, which are useful as central nervous system agents and are particularly useful as dopaminergic, serotonergic, antipsychotic, and anxiolytic agents.

10 Claims, No Drawings

SUBSTITUTED CYCLOHEXYLAMINES AS CENTRAL NERVOUS SYSTEMS AGENTS

This application is a 371 of PCT/US96/13687 filed Aug. 23, 1996 and this application claims the benefit of U.S. Provisional Application No. 60/004,193 filed Sep. 22, 1995.

BACKGROUND OF THE INVENTION

The present invention relates to novel substituted cyclohexylamines and derivatives thereof useful as pharmaceutical agents, to methods for their production, to pharmaceutical compositions which include these compounds and a pharmaceutically acceptable carrier, and to pharmaceutical methods of treatment. The novel compounds of the present invention are central nervous system agents. More particularly, the novel compounds of the present invention are both dopaminergic and serotonergic agents.

Compounds which interact with the dopamine D2 (DA D2) receptor have been shown to be efficacious in the treatment of psychiatric disorders such as schizophrenia. However, chronic administration of these agents causes various movement disorders both clinically and in animal models. It has been shown that administration of compounds that interact with the serotonin-1A (5-HT1A) receptor can block or prevent these extrapyramidal side effects in preclinical models (Neal-Beliveau B. S., et al., *J. Pharm. Exp. Ther.*, 1993;265:207–17). Increases in both dopamine D2 and 5-HT1A receptor densities have been observed during postmortem studies of schizophrenic brains (Hashimoto T., et al., *Life Sciences*, 1991;48:355–363 and references cited therein). Thus, it seems likely both DA D2 and 5-HT1A receptors play an important role in the etiology of schizophrenia. Taken together, these studies suggest that compounds having the ability to interact with both dopamine D2 and 5-HT1A receptors will have increased efficacy in the treatment of schizophrenia while causing less side effects. The compounds of the present invention have potent binding affinity for both the dopamine D2 receptor and the 5-HT1A receptor. They also show activity in a behavioral paradigm predictive of antipsychotic efficacy.

A series of substituted cyclohexanols and cyclohexylamines represented by the formula

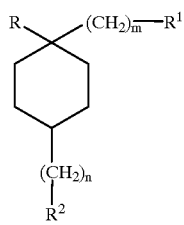

wherein R is $-OR^3$, wherein $R^3$ is hydrogen, lower alkyl, cycloalkyl, cycloalkylalkyl, aryl lower alkyl, lower alkanoyl, aroyl, or aryl lower alkanoyl;

wherein $R^4$ and $R^5$ are each independently hydrogen, lower alkyl, cycloalkyl, cycloalkylalkyl, aryl, heteroaryl, aryl lower alkyl, heteroaryl lower alkyl, lower alkanoyl, cycloalkanoyl, cycloalkylalkanoyl, aryl lower alkanoyl, heteroaryl lower alkanoyl, aroyl, heteroaroyl, or $R^4$ and $R^5$ are taken together with the nitrogen atom to which they are attached to form a ring denoted by

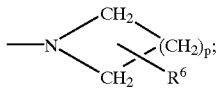

wherein p is zero or an integer from 1 to 4 and $R^6$ is hydrogen, lower alkyl, cycloalkyl, or cycloalkylalkyl

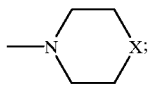

wherein X is oxygen or sulfur or

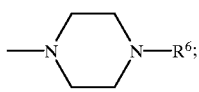

wherein $R^6$ is as defined above, or

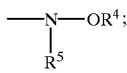

wherein $R^4$ and $R^5$ are each independently hydrogen, lower alkyl, cycloalkyl, cycloalkylalkyl, aryl, aryl lower alkyl, lower alkanoyl, aryl lower alkanoyl, aroyl, or $R^4$ and $R^5$ are taken together with the oxygen and nitrogen atoms to which they are attached to form a ring denoted by

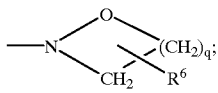

wherein
q is an integer from 2 to 3 and $R^6$ is as defined above;
m is zero or an integer from 1 to 2;
$R^1$ is hydrogen, aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower akyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;
n is zero or an integer from 1 to 4;
$R^2$ is

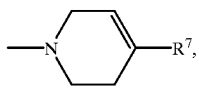 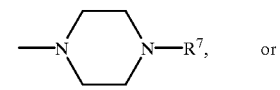 or

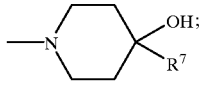

wherein $R^7$ is aryl, 2-, 3-, or 4-pyridinyl or 2-, 3-, or 4-pyridinyl substituted by lower alkyl, lower alkoxy, or halogen, 2-, 4-, or 5-pyrimidinyl or 2-, 4-, or 5-pyrimidinyl substituted by lower alkyl, lower alkoxy, or halogen, 2-pyrazinyl or 2-pyrazinyl substituted by lower alkyl, lower alkoxy, or halogen, 2- or 3-thienyl or 2- or 3-thienyl substituted by lower alkyl or halogen, 2- or 3-furanyl or 2- or 3-furanyl substituted by lower alkyl or halogen, 2-, 4-, or 5-thiazolyl or 2-, 4-, or 5-thiazolyl substituted by lower alkyl or halogen;

and the corresponding cis and trans isomers thereof; or a pharmaceutically acceptable acid addition salt thereof are disclosed in U.S. Pat. No. 5,047,406 as dopaminergic agents useful as antipsychotic and antihypertensive agents as well as for treating hyperprolactinaemia-related conditions and central nervous system disorders.

A series of 2-(4-phenyl-1-piperazinyl-alkyl)-aminopyrimidine derivatives represented by the formula

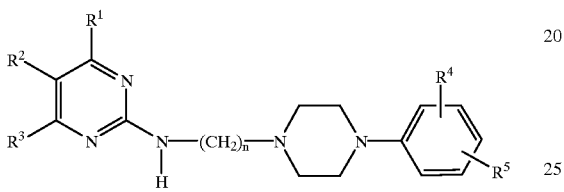

wherein $R^1$ and $R^3$ may be the same or different and independently represent hydrogen, halogen, an amino group, a hydroxyl group, a straight or branched chain lower alkyl group, a straight or branched chain lower alkoxy group, or a straight or branched chain hydroxy-lower alkyl group, $R^2$ represents hydrogen, halogen, a carboxyl group, a straight or branched chain lower alkyl group, a straight or branched chain lower alkylcarbonyl group, or a straight or branched chain lower alkyloxycarbonyl group, $R^4$ and $R^5$ may be the same or different and independently represent hydrogen, halogen, a straight or branched chain lower alkyl group, or a straight or branched chain lower alkoxy group, and n represents an integer of 2 to 6 or a pharmaceutically acceptable acid addition salt thereof are disclosed in U.S. Pat. No. 5,075,308 as therapeutic agents for urinary obstruction.

The compounds of the present invention, unlike the compounds disclosed in U.S. Pat. No. 5,047,406, interact with both the dopamine D2 and serotonergic 1A receptors. Thus, the compounds of the present invention are useful in the treatment of psychoses such as schizophrenia without the adverse extrapyramidal effects associated with an agent that interacts only with the dopamine receptor.

SUMMARY OF THE INVENTION

Accordingly, the present invention is a compound of Formula I

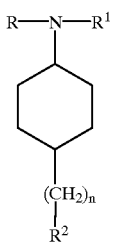

wherein R is heteroaryl;

$R^1$ is hydrogen, lower alkyl, cycloalkyl, aryl, or benzyl;
n is an integer from 1 to 2;
$R^2$ is

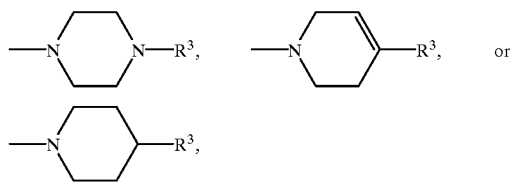

wherein $R^3$ is 2-pyrimidinyl,
2-pyrimidinyl substituted by 1 to 2 substituents selected from the group consisting of
lower alkyl,
lower alkoxy, and
halogen,
2-quinazolinyl,
4-quinazolinyl,
2-, 3-, or 4-pyridinyl,
2- or 3-thienyl,
2-thiazolyl,
2-pyrazinyl,
phenyl, or
phenyl substituted by 1 to 4 substituents selected from the group consisting of
lower alkyl,
lower alkoxy,
hydroxy, halogen, and
trifluoromethyl; and the corresponding cis and trans isomers thereof; or a pharmaceutically acceptable acid addition salt thereof.

As dopaminergic and serotonergic agents, the compounds of Formula I are useful as antipsychotic agents for treating psychoses such as schizophrenia. They are also useful as anxiolytic agents for the treatment of anxiety.

A still further embodiment of the present invention is a pharmaceutical composition for administering an effective amount of a compound of Formula I in unit dosage form in the treatment methods mentioned above.

Finally, the present invention is directed to methods for production of a compound of Formula I.

DETAILED DESCRIPTION OF THE INVENTION

In the compounds of Formula I, the term "lower alkyl" means a straight or branched hydrocarbon radical having from 1 to 6 carbon atoms and includes, for example, methyl, ethyl, n-propyl, isopropyl, n-butyl, sec-butyl, isobutyl, tert-butyl, n-pentyl, n-hexyl, and the like.

The term "cycloalkyl" means a three- to seven-member saturated hydrocarbon ring and includes, for example, cyclopropyl, cyclobutyl, cyclopentyl, cyclohexyl, cycloheptyl, and the like.

The term "aryl" means an aromatic radical which is a phenyl group or phenyl group substituted by 1 to 4 substituents selected from lower alkyl, lower alkoxy, hydroxy, halogen, or trifluoromethyl such as, for example, 4-fluorophenyl, 2-methoxyphenyl, 3-trifluoromethylphenyl, 2,3-dichlorophenyl, 2,3-dimethylphenyl, and the like.

The term "heteroaryl" means a heteroaromatic radical which is 2-, 3-, or 4-pyridinyl or 2- or 4-pyridinyl substituted by lower alkyl, lower alkoxy, or halogen, 2-, 4-, or 5-pyrimidinyl or 2-,4-, or 5-pyrimidinyl substituted by 1 to 3 substituents selected from lower alkyl, lower alkoxy, aryl, trifluoromethyl, or halogen, 2- or 4-quinazolinyl, 2-pyrazinyl, 2-thiazolyl, 2-benzothiazolyl or 2-benzothiazolyl substituted by lower alkyl, lower alkoxy or halogen, or 2-benzoimidazolyl or 2-benzoimidazolyl substituted by lower alkyl, lower alkoxy, or halogen.

"Lower alkoxy" is O-alkyl of from 1 to 6 carbon atoms as defined above for "lower alkyl."

"Halogen" is fluorine, chlorine, bromine, or iodine.

Pharmaceutically acceptable acid addition salts of the compounds of Formula I include salts derived from nontoxic inorganic acids, such as hydrochloric, nitric, phosphoric, sulfuric, hydrobromic, hydriodic, phosphorous, and the like, as well as the salts derived from nontoxic organic acids, such as aliphatic monoand dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts," *Journal of Pharmaceutical Science*, 1977;66:1–19).

The acid addition salts of said basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

The compounds of the present invention may exist as a mixture of cis and trans isomers or as the individual cis and trans isomers. The mixture of isomers as well as the individual isomers are intended to be encompassed within the scope of the present invention.

A preferred compound of Formula I is one wherein
R is 2-, 3-, or 4-pyridinyl,
  2-,3-, or 4-pyridinyl substituted by lower alkyl,
  2- or 4-pyrimidinyl,
  2- or 4-pyrimidinyl substituted by 1 to 2 substituents selected from lower alkyl, lower alkoxy, aryl, trifluoromethyl, or halogen,
  4-quinazolinyl,
  2-pyrazinyl,
  2-thiazolyl,
  2-benzothiazolyl,
  2-benzoimidazolyl, or
  2-benzoimidazolyl substituted by lower alkyl;
$R^1$ is hydrogen or methyl;
n is an integer of 2;

$R^2$ is

 or 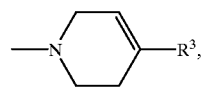, wherein $R^3$ is 2-pyrimidinyl,
  2-, 3-, or 4-pyridinyl,
  2- or 3-thienyl,
  2-thiazolyl,
  2-pyrazinyl,
  phenyl, or
  phenyl substituted by 1 to 4 substituents selected from the group consisting of
    lower alkyl,
    lower alkoxy,
    hydroxy, halogen, and
    trifluoromethyl.

Another preferred embodiment is a compound of Formula I wherein
R is 2-, 3-, or 4-pyridinyl,
  2-(3-methyl-pyridinyl),
  2- or 4-pyrimidinyl,
  2-(4-methyl-pyrimidinyl),
  2-(5-methyl-pyrimidinyl),
  2-(5-methoxy-pyrimidinyl),
  2-(5-phenyl-pyrimidinyl),
  2-(4-trifluoromethyl-pyrimidinyl),
  2-(5-fluoro-pyrimidinyl),
  2-(4,6-dimethyl-pyrimidinyl),
  4-quinazolinyl,
  2-pyrazinyl,
  2-thiazolyl,
  2-benzothiazolyl, or
  2-(1(N)-methyl-H-benzoimidazolyl);
$R^1$ is hydrogen or methyl;
n is an integer of 2;
$R^2$ is

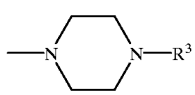 or 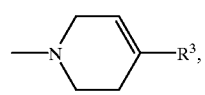, wherein $R^3$ is 2-pyrimidinyl,
  2-, 3-, or 4-pyridinyl,
  2- or 3-thienyl,
  2-thiazolyl,
  2-pyrazinyl,
  phenyl, or
  phenyl substituted by 1 to 2 substituents selected from the group consisting of
    lower alkyl,
    lower alkoxy,
    hydroxy, halogen, and
    trifluoromethyl.

Also preferred is a compound of Formula I wherein
R is 2-quinazolinyl, or
  4-quinazolinyl.

Particularly valuable are:
cis-{4-[2-(4-Pyridin-2-yl-piperazin-1-yl)-ethyl]-cyclohexyl}-pyrimidin-2-yl-amine hydrochloride;
trans-{4-[2-(4-Pyridin-2-yl-piperazin-1-yl)ethyl]-cyclohexyl}-pyrimidin-2-yl-amine;

trans-{4-[2-(4-Phenyl-piperazin-1-yl)-ethyl]-cyclohexyl}-pyrimidin-2-yl-amine;
trans-(4-{2-[4-(2,3-Dichloro-phenyl)-piperazin-1-yl]-ethyl}-cyclohexyl)-pyrimidin-2-yl-amine;
trans-(4-{2-[4-(2,3-Dichloro-phenyl)-piperazin-1-yl]-ethyl}-cyclohexyl)-methyl-pyrimidin-2-yl-amine;
trans-(4-{2-[4-(2,3-Dimethyl-phenyl)-piperazin-1-yl]-ethyl}-cyclohexyl)-pyrimidin-2-yl-amine;
trans-{4-[2-(4-Pyridin-2-yl-piperazin-1-yl)ethyl]-cyclohexyl}-quinazolin-4-yl-amine;
trans-{4-[2-(4-Phenyl-piperazin-1-yl)-ethyl]-cyclohexyl}-quinazolin-4-yl-amine;
cis-{4-[2-(4-Phenyl-piperazin-1-yl)-ethyl]-cyclohexyl}-quinazolin-4-yl-amine;
cis-{4-[2-(4-Phenyl-piperazin-1-yl)-ethyl]-cyclohexyl}-pyrimidin-2-yl-amine hydrochloride;
trans-Methyl-{4-[2-(4-phenyl-piperazin-1-yl)ethyl]-cyclohexyl}-pyrimidin-2-yl-amine;
trans-(5-Fluoro-pyrimidin-2-yl)-{4-[2-(4-phenyl-piperazin-1-yl)-ethyl]-cyclohexyl}-amine;
trans-Pyrimidin-2-yl-(4-{2-[4-(3-trifluoromethyl-phenyl)-piperazin-1-yl]-ethyl}-cyclohexyl)-amine;
trans-(4-{2-[4-(2-Methoxy-phenyl)-piperazin-1-yl]-ethyl}-cyclohexyl)-pyrimidin-2-yl-amine;
trans-Pyrimidin-2-yl-{4-[2-(4-pyrimidin-2-yl-piperazin-1-yl)-ethyl]-cyclohexyl}-amine;
trans-(4-{2-[4-(4-Fluoro-phenyl)-piperazin-1-yl]-ethyl}-cyclohexyl)-pyrimidin-2-yl-amine;
trans-{4-[2-(4-Phenyl-3,6-dihydro-2H-pyridin-1-yl)-ethyl]-cyclohexyl)}-pyrimidin-2-yl-amine;
trans-Pyrimidin-2-yl-{4-[2-(4-thiazol-2-yl-piperazin-1-yl)-ethyl]-cyclohexyl}-amine;
trans-(4-{2-[4-(4-Methoxy-phenyl)-piperazin-1-yl]-ethyl}-cyclohexyl)-pyrimidin-2-yl-amine;
trans-Pyrimidin-2-yl-{4-[2-(2,3,5,6-tetrahydro-[1,2']bipyrazinyl-4-yl)-ethyl]-cycohexyl}-amine;
trans-{4-[2-(4-Pyridin-3-yl-piperazin-1-yl)-ethyl]-cyclohexyl}-pyrimidin-2-yl-amine;
trans-{4-[2-(3,4-Dihydro-1H-isoquinolin-2-yl)-ethyl]-cyclohexyl}-pyrimidin-2-yl-amine;
trans-4-(4-{2-[4-(Pyrimidin-2-ylamino)-cyclohexyl]-ethyl}-piperazin-1-yl)-phenol;
trans-{4-[2-(4-Phenyl-piperazin-1-yl)-ethyl]-cyclohexyl}-pyridin-3-yl-amine;
trans-{4-[2-(4-Phenyl-piperazin-1-yl)-ethyl]-cyclohexyl}-pyridin-2-yl-amine;
trans-(4-Methyl-pyrimidin-2-yl)-{4-[2-(4-phenyl-piperazin-1-yl)-ethyl]-cyclohexyl}-amine;
trans-{4-[2-(4-Phenyl-piperazin-1-yl)-ethyl]-cyclohexyl}-thiazol-2-yl-amine;
trans-{4-[2-(4-Phenyl-piperazin-1-yl)-ethyl]-cyclohexyl}-pyrazin-2-yl-amine;
trans-Benzothiazol-2-yl-{4-[2-(4-phenyl-piperazin-1-yl)-ethyl]-cyclohexyl}-amine;
cis-(1-Methyl-1H-benzoimidazol-2-yl)-{4-[2-(4-phenyl-piperazin-1-yl)-ethyl]-cyclohexyl}-amine;
trans-(1-Methyl-1H-benzoimidazol-2-yl)-{4-[2-(4-phenyl-piperazin-1-yl)-ethyl]-cyclohexyl}-amine;
trans-{4-[2-(4-Phenyl-piperazin-1-yl)-ethyl]-cyclohexyl}-pyrimidin-4-yl-amine;
trans-(3-Methyl-pyridin-2-yl)-{4-[2-(4-phenyl-piperazin-1-yl)-ethyl]-cyclohexyl}-amine;
trans-{4-[2-(4-Phenyl-piperazin-1-yl)-ethyl]-cyclohexyl}-pyridin-4-yl-amine;
trans-{4-[2-(4-Phenyl-piperazin-1-yl)-ethyl]-cyclohexyl}-4-trifluoromethyl-pyrimidin-2-yl)-amine;
trans-(5-Methoxy-pyrimidin-2-yl)-{4-[2-(4-phenyl-piperazin-1-yl)-ethyl]-cylohexyl}-amine;
trans-(5-Methyl-pyrimidin-2-yl-{4-[2-(4-phenyl-piperazin-1-yl)-ethyl]-cyclohexyl}-amine;
trans-(5-Phenyl-pyrimidin-2-yl-{4-[2-(4-phenyl-piperazin-1-yl)-ethyl]-cyclohexyl}-amine; and
trans-(4,6-Dimethyl-pyrimidin-2-yl-{4-[2-(4phenyl-piperazin-1-yl)-ethyl]-cyclohexyl}-amine; or a pharmaceutically acceptable acid addition salt thereof.

Most particularly valuable is:
trans-{4-[2-(4-Phenyl-piperazin-1-yl)-ethyl]-cyclohexyl}-pyrimidin-2-yl-amine; or a pharmaceutically acceptable acid addition salt thereof.

The compounds of Formula I are valuable dopaminergic and serotonergic agents. The tests employed indicate that compounds of Formula I possess dopaminergic and serotonergic activity. Thus, the compounds of Formula I were tested for their ability to inhibit spontaneous locomotor activity in mice, a test predictive of antipsychotic activity, according to the assay described by McLean J. R., et al., *Pharmacology, Biochemistry and Behavior*, 1978;8:97–99; for their ability to bind to the dopamine D2 receptor using [$^3$H]-2-(N-propyl-N-2-thienylethylamino)-5-hydroxytetralin ([$^3$H]N-0437) as the ligand according to the method disclosed in Van der Weide J., et al., *Eur. J. Pharmacol.*, 1987;134:211–219; and for their ability to bind to the serotonin 5HT1A receptor using [$^3$H]-8-hydroxy-dipropylaminotetralin ([$^3$H]-8-OH-DPAT) as the ligand according to the method disclosed in Peroutka S. J., et al., *Brain Res.*, 1985;344:167–171. The above test methods are incorporated herein by reference. The data in the table show the dopaminergic and serotonergic activity of representative compounds of Formula I.

| | | Biological Activity of Compounds of Formula I | | |
|---|---|---|---|---|
| Example No. | Compound | Inhibition of [$^3$H]N-0437 Binding to h-D2 Receptors ($K_i$, nM) | Inhibition of [$^3$H]8-OH-DPAT Binding to Rat Hippocampus Membranes ($K_i$, nM) | Inhibition of Locomotor Activity in Mice ($ED_{50}$, mg/kg, IP) |
| 1 | cis-{4-[2-(4-Pyridin-2-yl-piperazin-1-yl)-ethyl]-cyclohexyl}-pyrimidin-2-yl-amine hydrochloride | 46 | 8.8 | 1.2 |

-continued

Biological Activity of Compounds of Formula I

| Example No. | Compound | Inhibition of [$^3$H]N-0437 Binding to h-D2 Receptors ($K_i$, nM) | Inhibition of [$^3$H]8-OH-DPAT Binding to Rat Hippocampus Membranes ($K_i$, nM) | Inhibition of Locomotor Activity in Mice ($ED_{50}$, mg/kg, IP) |
|---|---|---|---|---|
| 1a | trans-{4-[2-(4-Pyridin-2-yl-piperazin-1-yl)-ethyl]-cyclohexyl}-pyrimidin-2-yl-amine | 12 | 2.2 | 0.24 |
| 2 | trans-{4-[2-(4-Phenyl-piperazin-1-yl)-ethyl]-cyclohexyl}-pyrimidin-2-yl-amine | 3.4 | 3.1 | 0.3 |
| 9 | cis-{4-[2-(4-Phenyl-piperazin-1-yl)-ethyl]-cyclohexyl}-pyrimidin-2-yl-amine hydrochloride | 28 | 1.9 | |
| 12 | trans-Pyrimidin-2-yl-(4-{2-[4-(3-trifluoromethyl-phenyl}-piperazin-1-yl]-ethyl]-cyclohexyl)-amine | 6 | 13 | 4.4 |
| 13 | trans-(4-{2-[4-(2-Methoxy-phenyl)-piperazin-1-yl]-ethyl}-cyclohexyl)-pyrimidin-2-yl-amine | 3 | 0.5 | 0.5 |
| 15 | trans-(4-{2-[4-(4-Fluoro-phenyl)-piperazin-1-yl]-ethyl}-cyclohexyl)-pyrimidin-2-yl-amine | 8.3 | 4.4 | 0.7 |
| 16 | trans-{4-[2-(4-Phenyl-3,6-dihydro-2H-pyridin-1-yl)-ethyl]-cyclohexyl}-pyrimidin-2-yl-amine | 4.7 | 3.9 | 0.25 |
| 17 | trans-Pyrimidin-2-yl-{4-[2-(4-thiazol-2-yl-piperazin-1-yl)-ethyl]-cyclohexyl}-amine | 46 | 10 | 0.3 |
| 20 | trans-{4-[2-(4-Pyridin-3-yl-piperazin-1-yl)-ethyl]-cyclohexyl)-pyrimidin-2-yl-amine | 25.3 | 9.5 | — |
| 24 | trans-{4-[2-(4-Phenyl-piperazin-1-yl)-ethyl]-cyclohexyl}-pyridin-2-yl-amine | 1.4 | 1.2 | 0.2 |
| 26 | trans-{4-[2-(4-Phenyl-piperazin-1-yl)-ethyl]-cyclohexyl}-thiazol-2-yl-amine | 2.35 | 7.9 | — |
| 27 | trans-{4-[2-(4-Phenyl-piperazin-1-yl)-ethyl]-cyclohexyl)-pyrazin-2-yl-amine | 0.93 | 5.1 | 0.18 |

A compound of Formula I

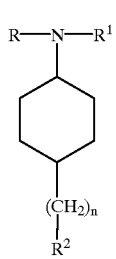

wherein R is heteroaryl;
R$^1$ is hydrogen,
  lower alkyl,
  cycloalkyl,
  aryl, or
  benzyl;
n is an integer from 1 to 2;

R$^2$ is

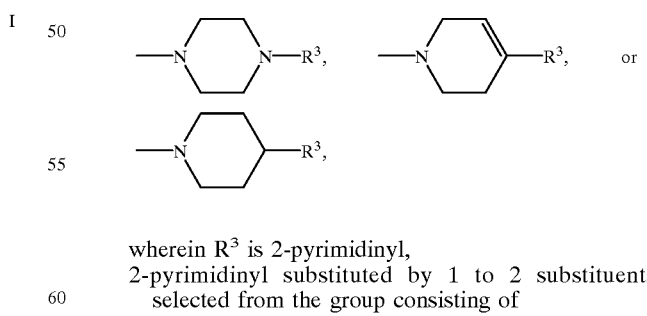

wherein R$^3$ is 2-pyrimidinyl,
  2-pyrimidinyl substituted by 1 to 2 substituents selected from the group consisting of
    lower alkyl,
    lower alkoxy, and
    halogen,
  2-quinazolinyl,
  4-quinazolinyl,
  2-, 3-, or 4-pyridinyl,
  2- or 3-thienyl, 2-thiazolyl,
2-pyrazinyl,
phenyl, or
phenyl substituted by 1 to 4 substituents selected from the group consisting of
lower alkyl,
lower alkoxy,
hydroxy, halogen, and
trifluoromethyl; and the corresponding cis and trans isomers thereof; or a pharmaceutically acceptable acid addition salt thereof may be prepared by reacting a compound of Formula II

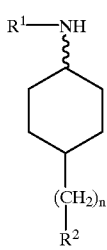

II wherein $R^1$, n, and $R^2$ are as defined above with a compound of Formula III

RX  III wherein X is Cl or Br and R is as defined above in the presence of a base such as, for example, triethylamine and the like and a solvent such as, for example, ethanol and the like at about room temperature to the reflux temperature of the solvent to give a compound of Formula I. Preferably, the reaction is carried out in the presence of triethylamine in ethanol at reflux temperature.

A compound of Formula II is prepared from a compound of Formula IV

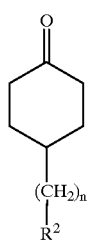

IV wherein n and $R^2$ are as defined above and a compound of Formula V $R^1NH_2$  V wherein $R^1$ is as defined above in the presence of a metal hydride such as, for example, sodium cyanoborohydride and the like in acetic acid and a solvent such as, for example, methanol and the like to give a compound of Formula II. Preferably, the reaction is carried out in the presence of sodium cyanoborohydride in acetic acid and methanol.

A compound of Formula IV is prepared from a compound of Formula VI

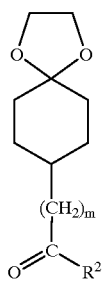

VI wherein m is zero or an integer of 1 and $R^2$ is as defined above in the presence of a metal hydride such as, for example, aluminum hydride and the like in a solvent such as, for example, tetrahydrofuran and the like to give after subsequent treatment of the intermediate compound with an acid such as, for example, aqueous hydrochloric acid and the like in a solvent such as, for example, acetone and the like to remove the ketal group a compound of Formula IV. Preferably, the reaction is carried out in the presence of aluminum hydride in tetrahydrofuran followed by treatment with aqueous hydrochloric acid in acetone to remove the ketal group.

A compound of Formula VI is prepared from a compound of Formula VII

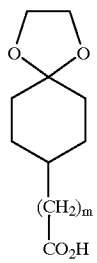

VII wherein m is as defined above and a compound of Formula VIII $R^2H$  VIII wherein $R^2$ is as defined above in the presence of isobutyl chloroformate and the like, and a base such as, for example, triethylamine and the like and a solvent such as, for example, methylene chloride and the like to give a compound of Formula VI. Preferably, the reaction is carried out in the presence of isobutyl chloroformate and triethylamine in the methylene chloride.

A compound of Formula I may exist as a mixture of cis or trans isomers or as the separate cis or trans isomer. Accordingly, as another aspect of the present invention, a mixture of cis and trans isomers of Formula I may be separated into the individual cis or trans isomer by conventional methodology such as, for example, by fractional crystallization, chromatography and the like.

Preferably, the trans isomer of a compound of Formula I

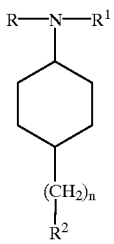   I wherein R, R¹, n, and R² are as defined above may be prepared by reacting a compound of Formula IX

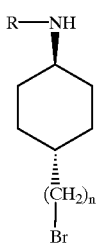   IX wherein R and n are as defined above and a compound of Formula VIII

R²H   VIII wherein R² is as defined above in the presence of a base such as, for example, potassium carbonate and the like in a solvent such as, for example, acetonitrile and the like to give the trans isomer of a compound of Formula I. Preferably, the reaction is carried out in the presence of potassium carbonate in acetonitrile.

A compound of Formula IX is prepared from a compound of Formula X

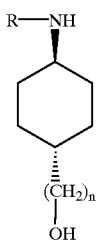   X wherein R and n are as defined above in the presence of polymer supported triphenylphosphine and carbon tetrabromide in a solvent such as, for example, methylene chloride and the like to give a compound of Formula IX. Preferably, the reaction is carried out in the presence of polymer supported triphenylphosphine and carbon tetrabromide in methylene chloride.

A compound of Formula X is prepared from a compound of Formula XI

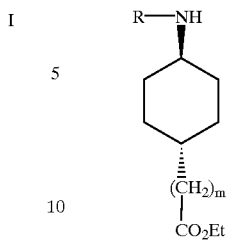   XI wherein R and m are as defined above in the presence of a metal hydride such as, for example, lithium aluminum hydride and the like in a solvent such as, for example, tetrahydrofuran and the like to give a compound of Formula X. Preferably, the reaction is carried out in the presence of lithium aluminum hydride in tetrahydrofuran.

A compound of Formula XI is prepared from a compound of Formula XII

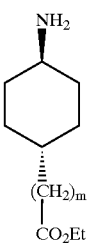   XII wherein m is as defined above and a compound of Formula III

RX   III wherein R and X are as defined above in the presence of a base such as, for example, triethylamine and the like in a solvent such as, for example, ethanol and the like at about room temperature to the reflux temperature of the solvent to give a compound of Formula XI. Preferably, the reaction is carried out in the presence of triethylamine in ethanol at reflux temperature.

Preferably, the trans isomer of a compound of Formula Ia

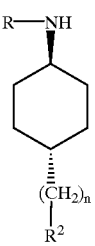   Ia wherein R, R², and n are as defined above may be prepared from a compound of Formula IV

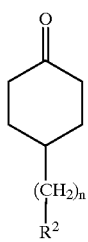

IV wherein n and $R^2$ are as defined above and a compound of Formula XIII

XIII wherein R is as defined above using methodology used to prepare a compound of Formula II from a compound of Formula IV and a compound of Formula V followed by separation of the isomers using conventional methodology such as, for example, chromatography, crystallization, and the like to afford a compound of Formula Ia.

Preferably, the trans isomer of a compound of Formula Ib

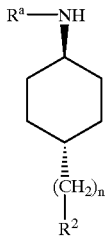

Ib wherein $R^a$ is 2- or 5-pyrimidinyl substituted by trifluoromethyl or halogen and $R^2$ and n are as defined above may be prepared from a compound of Formula XIV

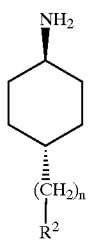

XIV wherein $R^2$ and n are as defined above and a compound of Formula XV

XV wherein $R^a$ and X are as defined above using the methodology used to prepare a compound of Formula I from a compound of Formula II and a compound of Formula III to afford a compound of Formula Ib.

A compound of Formula XIV is prepared from a compound of Formula XVI

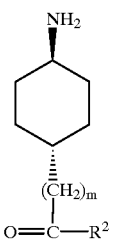

XVI wherein $R^2$ and n are as defined above using the methodology used to prepare a compound of Formula IV from a compound of Formula VI to afford a compound of Formula XIV.

A compound of Formula XVI is prepared from a compound of Formula XVII

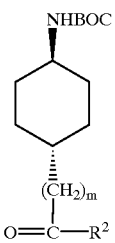

XVII wherein BOC is tert-butoxycarbonyl and $R^2$ and m are as defined above in the presence of an acid such as, for example, hydrochloric acid and the like to afford a compound of Formula XVI.

A compound of Formula XVII is prepared from a compound of Formula XVIII

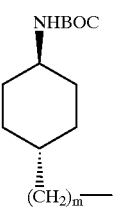

XVIII wherein BOC and m are as defined above and a compound of Formula VIII in the presence of a coupling reagent such as, for example, 1-ethyl-(3-dimethylaminopropyl)-carbodiimide hydrochloride and the like and a base such as, for example, triethylamine and the like to afford a compound of Formula XVII.

A compound of Formula XVIII is prepared by treating 4-nitrophenyl acetic acid with hydrogen in the presence of a catalyst such as, for example, Raney nickel and the like and a base such as, for example, sodium hydroxide to afford the 4-aminocyclohexane acetic acid which is treated in situ with di-tert-butyl dicarbonate and the like in a solvent such as, for example, tetrahydrofuran and the like to afford a compound of Formula XVIII.

Preferably, the trans isomer of a compound of Formula Ic

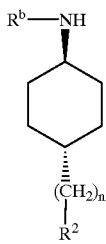

Ic wherein $R^b$ is 2-pyrimidinyl substituted by lower alkyl, lower alkoxy, aryl, or trifluoromethyl and $R^2$ and n are as defined above may be prepared from a compound of Formula XIX

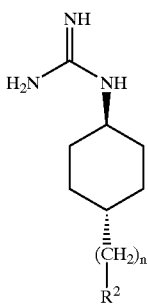

XIX wherein $R^2$ and n are as defined above and a compound of Formula XX or a compound of Formula XXI

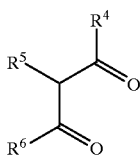

XX or

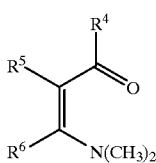

XXI wherein $R^4$, $R^5$, and $R^6$ are each independently the same or different and are lower alkyl, lower alkoxy, aryl, or trifluoromethyl in the presence of a base such as, for example, sodium methoxide (NaOMe) and the like and a solvent such as, for example, methanol and the like to afford a compound of Formula Ic.

A compound of Formula XIX is prepared from a compound of Formula XXII

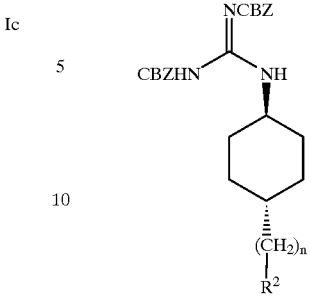

XXII wherein CBZ is carbobenzyloxy and $R^2$ and n are as defined above by treatment with hydrogen in the presence of a catalyst such as, for example, palladium on carbon and the like to afford a compound of Formula XIX.

A compound of Formula XXII is prepared from a compound of Formula XIV and S-methyl-$N,N^1$-dicarbobenzyloxy isothiourea in the presence of a base such as, for example, triethylamine and the like and a solvent such as, for example, dimethylformamide and the like to afford a compound of Formula XXII.

Compounds of Formula III, Formula V, Formula VII, Formula VIII, Formula XII, Formula XIII, Formula XV, Formula XX, and Formula XXI are either known or capable of being prepared by methods known in the art.

The compounds of the present invention can be prepared and administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

In therapeutic use as antipsychotic and anxiolytic agents, the compounds utilized in the pharmaceutical method of this invention are administered at the initial dosage of about 1 mg to about 50 mg per kilogram daily. A daily dose range of about 5 mg to about 25 mg per kilogram is preferred. The dosages, however, may be varied depending upon the requirements of the patient, the severity of the condition being treated, and the compound being employed. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The following nonlimiting examples illustrate the inventors' preferred methods for preparing the compounds of the invention.

EXAMPLE 1 cis-{4-[2-(4-Pyridin-2-yl-piperazin-1-yl)-ethyl]-cyclohexyl}-pyrimidin-2-yl-amine hydrochloride
and EXAMPLE 1a trans-{4-[2-(4-Pyridin-2-yl-piperazin-1-yl)-ethyl]-cyclohexyl}-pyrimidin-2-yl-amine
Step 1: Preparation of 2-(1,4-Dioxaspiro[4.5]dec-8yl)-1-[4-(2-pyridinyl)-1-piperazinyl]-ethanone A solution of (1,4-Dioxaspiro[4.5]dec-8-yl)-acetic acid (U.S. Pat. No. 5,124,332) (20.0 g, 99.8 mmol) and triethylamine (21 mL, 149 mmol) in 200 mL of methylene chloride ($CH_2Cl_2$) was cooled to 0° C. in an ice bath and treated with isobutyl chloroformate (13.98 mL, 107.8 mmol). After stirring for 10 minutes 1-(2-pyridinyl)piperazine (17.6 g, 108 mmol) is added in 50 mL of methylene chloride. The reaction is removed from the ice bath and stirred at room temperature for 24 hours. The reaction mixture is treated with 200 mL of a saturated sodium bicarbonate solution. The aqueous layer is separated and extracted with an additional 150 mL of methylene chloride. The combined organic fractions are dried over magnesium sulfate ($MgSO_4$), and the solvent is removed under reduced pressure to give an oil which is triturated with diethyl ether ($Et_2O$) to give 2-(1,4-dioxaspiro[4.5]dec-8-yl)-1-[4-(2-pyridinyl)-1-piperazinyl]-ethanone (22.7 g) as a white solid.

Step 2: Preparation of 4-[2-[4-(2-Pyridinyl)-1-piperazinyl]ethyl]-cyclohexanone

A slurry of lithium aluminum hydride ($LiAlH_4$) (7.48 g, 197 mmol) in 180 mL of tetrahydrofuran (THF) is cooled to 0° C. and treated with aluminum chloride ($AlCl_3$) (8.76 g, 65.7 mmol) in 180 mL of diethyl ether. The reaction is stirred for 30 minutes and the 2-(1,4dioxaspiro[4.5]dec-8-yl)-1-[4-(2-pyridinyl)-1-piperazinyl]-ethanone (22.7 g, 65.7 mmol) was added in portions over 1 hour. The reaction is allowed to stir for 18 hours and is quenched with 8 mL of water and 18 mL of a 50% sodium hydroxide (NaOH) solution. The reaction is stirred for 1 hour and filtered through a pad of Celite. The filter cake is washed with 300 mL of diethyl ether. The combined organic extracts are concentrated to give a white solid which is dissolved in a 230 mL of a 1:1 mixture of acetone and 10% aqueous hydrochloric acid (HCl) solution. After stirring at room temperature for 60 hours, the acetone is removed under reduced pressure, and the pH of the reaction mixture is adjusted to pH 9 with concentrated ammonium hydroxide solution. The aqueous mixture is extracted with two 250 mL portions of chloroform, and the combined organic fractions are dried with sodium sulfate. The solvents are removed under reduced pressure, and the residue is triturated with diethyl ether to give 14.3 g 4-[2-[4-(2-pyridinyl)-1-piperazinyl]ethyl]-cyclohexanone as a white solid.

Step 3: Preparation of mixture of cis and trans-4-[2-[4-(2-pyridinyl)-1-piperazinyl]-ethyl]-cyclohexanamines A mixture of 4-[2-[4-(2-pyridinyl)-1-piperazinyl]ethyl]-cyclohexanone (10 g, 36.31 mmol) and ammonium acetate (27.2 g, 360 mmol) are dissolved in 250 mL methanol (MeOH). The solution is treated with sodium cyanoborohydride (1.62 g, 25.9 mmol) and stirred at room temperature for 18 hours. The solvent is removed under reduced pressure, and the residue is partitioned between chloroform and 2N sodium carbonate ($Na_2CO_3$) solution. The organic layer is separated, dried over sodium sulfate, and the solvents are removed under reduced pressure to give 10.0 g of a mixture of cis and trans-4-[2-[4-(2-pyridinyl)-1-piperazinyl]ethyl]-cyclohexanamines as a colorless oil which was used without further purification.

Step 4: Preparation of cis and trans-{4-[2-(4-pyridin-2-yl-piperazin-1-yl)ethyl]-cyclohexyl}-pyrimidin-2-yl-amine The mixture of cis and trans-4-[2-[4-(2-pyridinyl)-1-piperazinyl]ethyl]-cyclohexanamines (1.95 g, 7.05 mmol), 2-chloro-pyrimidine (0.56 g, 7.05 mmol) and triethylamine (0.9 mL) is heated to reflux for 32 hours. The reaction is cooled and the solvents removed under reduced pressure. The residue is partitioned between chloroform and 2N sodium carbonate solution. The organic layer is separated, dried over sodium sulfate, and the solvents are removed under reduced pressure. The residue is chromatographed over silica gel using a mixture of chloroform, methanol, and ammonia as the solvents. The separated cis isomer was isolated as the hydrochloride salt; mp 156° C.

The separated trans isomer was recrystallized from ethyl acetate to afford the title compound; mp 140° C.

In a process analogous to Example 1 and Example 1a using appropriate starting materials, the corresponding compounds of Formula I (Examples 2–11) are prepared as follows:

EXAMPLE 2 trans-{4-[2-(4-Phenyl-piperazin-1-yl)-ethyl] cyclohexyl}-pyrimidin-2-yl-amine; mp 162° C.

EXAMPLE 3 trans-(4-{2-[4-(2,3-Dichloro-phenyl)-piperazin-1-yl] ethyl}-cyclohexyl)-pyrimidin-2-yl-amine; mp 170° C.

EXAMPLE 4 trans-(4-{2-[4-(2,3-Dichloro-phenyl)-piperazin-1-yl] ethyl}-cyclohexyl)-methyl-pyrimidin-2-yl-amine; mp 95° C.

EXAMPLE 5 trans-(4-{2-[4-(2,3-Dimethyl-phenyl)-piperazin-1-yl] ethyl}-cyclohexyl)-pyrimidin-2-yl-amine; mp 167° C.

EXAMPLE 6 trans-{4-[2-(4-Pyridin-2-yl-piperazin-1-yl)-ethyl]-cyclohexyl}-quinazolin-4-yl-amine; mp 188° C.

EXAMPLE 7 trans-{4-[2-(4-Phenyl-piperazin-1-yl)-ethyl]-cyclohexyl}-quinazolin-4-yl-amine; mp 192° C.

EXAMPLE 8 cis-{4-[2-(4-Phenyl-piperazin-1-yl)-ethyl]-cyclohexyl}-quinazolin-4-yl-amine; mp 138° C.

EXAMPLE 9 cis-{4-[2-(4-Phenyl-piperazin-1-yl)-ethyl]-cyclohexyl}-pyrimidin-2-yl-amine hydrochloride; mp 120° C.

EXAMPLE 10 trans-Methyl-{4-[2-(4-phenyl-piperazin-1-yl)-ethyl]-cyclohexyl}-pyrimidin-2-yl-amine; mp 134° C.

EXAMPLE 11 trans-(5-Fluoro-pyrimidin-2-yl)-{4-[2-(4-phenyl-piperazin-1-yl)-ethyl]-cyclohexyl}-amine; mp 176° C.

EXAMPLE 12 trans-Pyrimidin-2-yl-(4-{2-[4-(3-trifluoromethyl-phenyl)-piperazin-1-yl]-ethyl}-cyclohexyl-amine Step 1: Preparation of trans-[4-(pyrimidin-2-yl-amino)-cyclohexyl]acetic acid ethyl ester A solution of trans-(4-Amino-cyclohexyl)-acetic acid ethyl ester (Karapavicius K., Palaima A. I., Knunyants I. L., Izv. Akad. Nauk SSSR, Ser. Khim., 1980;10;2374–9) (3.46 g, 18.7 mmol), 2-chloropyrimidine (2.14 g, 18.7 mmol) and triethylamine (5.21 mL) is refluxed in ethanol (EtOH) (10 mL) for 48 hours. The reaction is cooled, and the solvents are removed under reduced pressure. The residue is partitioned between chloroform and 2N aqueous sodium carbonate solution. The organic layer is separated, dried over sodium sulfate, and the solvents are removed under reduced pressure. The residue is chromatographed over silica gel using a mixture of chloroform and methanol to give trans-[4-(pyrimidin-2-ylamino)-cyclohexyl]-acetic acid ethyl ester.

Step 2: Preparation of trans-2-[4-(pyrimidin-2-ylamino)-cyclohexyl]-ethanol

A suspension of lithium aluminum hydride (0.45 g, 11.85 mmol) is cooled in an ice water bath and treated with a solution of trans-[4-(pyrimidin-2-ylamino)-cyclohexyl]-acetic acid ethyl ester (2.09 g, 7.9 mmol) in THF (15 mL) over 20 minutes. After stirring for 5 minutes, the ice bath is removed, and the reaction is stirred for an additional 40 minutes. The reaction is quenched with water, and sodium hydroxide is added. The mixture is stirred for 1 hour and is filtered through Celite and the filtrate evaporated to give trans-2-[4-(pyrimidin-2-ylamino)-cyclohexyl]-ethanol which is used without further purification.

Step 3: Preparation of trans-[4-(2-Bromoethyl)-cyclohexyl]-pyrimidin-2-yl-amine

A mixture of trans-2-[4-(pyrimidin-2-ylamino)-cyclohexyl]-ethanol (1.51 g, 6.9 mmol) is dissolved in a solution of methylene chloride (25 mL) containing polymer supported triphenylphosphine (2.87 g, approx 8.6 mmol). The mixture is cooled in an ice water bath, and carbon tetrabromide (2.3 g, 7.0 mmol) is added. The reaction is stirred for 1 hour, and the polymeric material was removed by filtration. The filtrate is concentrated and chromatographed on silica gel using a 2:1 mixture of chloroform and ethyl acetate (EtOAc) as the solvent to give trans-[4-(2-Bromoethyl)-cyclohexyl]-pyrimidin-2-yl-amine.

Step 4: Preparation of trans-Pyrimidin-2-yl-(4-{2-[4-(3-trifluoromethyl-phenyl)-piperazin-1-yl]-ethyl}-cyclohexyl)-amine A mixture of trans-[4-(2-Bromoethyl)-cyclohexyl]-pyrimidin-2-yl-amine (0.26 g, 0.91 mmol), 1-(3-trifluoromethyl-phenyl)-piperazine (0.21 g, 0.91 mmol), and potassium carbonate (0.21 g, 1.5 mmol) was heated in 10 mL refluxing acetonitrile for 18 hours. The reaction was diluted with methylene chloride, filtered, and the solvents were removed under reduced pressure. The residue was partitioned between chloroform and aqueous 2N sodium carbonate solution. The organic layer was dried over sodium sulfate and evaporated. The resulting residue was recrystallized from acetonitrile to give the title compound; mp 167° C.

In a process analogous to Example 12 using appropriate starting materials, the corresponding compounds of Formula I (Examples 13–21) are prepared as follows:

EXAMPLE 13 trans-(4-{2-[4-(2-Methoxy-phenyl)-piperazin-1-yl] ethyl}-cyclohexyl)-pyrimidin-2-yl-amine; mp 139° C.

EXAMPLE 14 trans-Pyrimidin-2-yl-{4-[2-(4-pyrimidin-2-yl-piperazin-1-yl)-ethyl]-cyclohexyl}-amine; mp 154° C.

EXAMPLE 15 trans-(4-{2-[4-(4-Fluoro-phenyl)-piperazin-1-yl]-ethyl}-cyclohexyl)-pyrimidin-2-yl-amine; mp 162° C.

EXAMPLE 16 trans-{4-[2-(4-Phenyl-3,6-dihydro-2H-pyridin-1-yl)-ethyl]-cyclohexyl}-pyrimidin-2-yl-amine; mp 146° C.

EXAMPLE 17 trans-Pyrimidin-2-yl-{4-[2-(4-thiazol-2-yl-piperazin-1-yl)-ethyl]-cyclohexyl}-amine; mp 151° C.

EXAMPLE 18 trans-(4-{2-[4-(4-Methoxy-phenyl)-piperazin-1-yl]-ethyl}-cyclohexyl)-pyrimidin-2-yl-amine; mp 177° C.

EXAMPLE 19 trans-Pyrimidin-2-yl-{4-[2-(2,3,5,6-tetrahydro[1,2']-1bipyrazinyl-4-yl)-ethyl]-cyclohexyl}-amine; mp 162° C.

EXAMPLE 20 trans-{4-[2-(4-Pyridin-3-yl-piperazin-1-yl)-ethyl]-cyclohexyl}-pyrimidin-2-yl-amine; mp 174–175° C.

EXAMPLE 21 trans-{4-[2-(3,4-Dihydro-1H-isoquinolin-2-yl)-ethyl]-cyclohexyl}-pyrimidin-2-yl-amine; mp 121–122° C.

EXAMPLE 22 trans-4-(4-{2-[4-(Pyrimidin-2-ylamino)-cyclohexyl]-ethyl}-piperazin-1-yl)-phenol A solution of trans-Pyrimidin-2-yl-{4-[2-(2,3,5,6tetrahydro[1,2']bipyrazinyl-4-yl)-ethyl]-cyclohexyl}-amine (Example 19) in 10 mL of 48% HBr was heated to reflux for 2 hours. The solution was evaporated under reduced pressure and then suspended in an aqueous solution which was adjusted to pH 8 by the addition of sodium hydroxide. The aqueous suspension was extracted with chloroform, and the organic solution was dried over sodium sulfate and the solvents removed under reduced pressure. The resulting residue was recrystallized from acetonitrile to give the title compound as an off-white solid; mp 192–194° C.

EXAMPLE 23

{4-[2-(4-Phenyl-piperazin-1-yl)-ethyl]-cyclohexyl}-pyridin-3-yl-amine

3-Aminopyridine (1.6 g, 16.9 mmol) and the ketone 4-[2-(4-phenyl-piperazin-1-yl)-ethyl]-cyclohexanone (1.09 g, 3.8 mmol) were heated together in toluene (20 mL) under reflux through 4A molecular sieves (25 g) for 16 hours. The resultant solution of imine intermediate was cooled to room temperature and stirred while a freshly prepared solution of sodium cyanoborohydride (0.97 g, 15.4 mmol) in methanol (15 mL) was quickly added. Acetic acid (0.6 mL) was then added dropwise (Caution: gas evolution). After 2.5 hours at room temperature, the reduction was quenched by the addition of 10% aqueous solution of $Na_2CO_3$ (75 mL). The mixture was vigorously stirred for 40 minutes, then extracted with diethyl ether (150 mL, 2×60 mL. The extract was dried over $MgSO_4$ and concentrated under vacuum. The residue (1.49 g) was heated at 90° C. under vacuum (2 mm-Hg) to remove the bulk of the excess 3-aminopyridine to leave predominantly a 3:1 mixture of trans and cis isomers of the product. Recrystallization from ethyl acetate (~10 mL)/diethyl ether (~50 mL) afforded 0.56 g (9:1 trans/cis). A second recrystallization from ethyl acetate (~10 mL) afforded the pure trans (0.42 g); mp 159–160° C.

In a process analogous to Example 23 using appropriate starting materials, the corresponding compounds of Formula I (Examples 24–33) are prepared as follows:

EXAMPLE 24 trans-{4-[2-(4-Phenyl-piperazin-1-yl)-ethyl] cyclohexyl}-pyridin-2-yl-amine; mp 136–138° C.

EXAMPLE 25 trans-(4-Methyl-pyrimidin-2-yl)-{4-[2-(4-phenyl-perazin-1-yl)-ethyl]-cyclohexyl}-amine; mp 147–148° C.

EXAMPLE 26 trans-{4-[2-(4-Phenyl-piperazin-1-yl)-ethyl]-cyclohexyl}-thiazol-2-yl-amine; mp 156–157° C.

EXAMPLE 27 trans-{4-[2-(4-Phenyl-piperazin-1-yl)-ethyl]-cyclohexyl}-pyrazin-2-yl-amine; mp 139–140° C.

EXAMPLE 28 trans-Benzothiazol-2-yl-{4-[2-(4-phenyl-piperazin-1-yl)-ethyl]-cyclohexyl}-amine; mp 187–188° C.

EXAMPLE 29 cis-(1-Methyl-1H-benzoimidazol-2-yl)-{4-[2-(4-phenyl-piperazin-1-yl)-ethyl]-cyclohexyl}-amine; mp 124–127° C.

EXAMPLE 30 trans-(1-Methyl-1H-benzoimidazol-2-yl)-{4-[2-(4-phenyl-piperazin-1-yl)-ethyl]-cyclohexyl}-amine; mp 162–163° C.

EXAMPLE 31 trans-{4-[2-(4-Phenyl-piperazin-1-yl)-ethyl]-cyclohexyl}-pyrimidin-4-yl-amine; mp 171° C.

EXAMPLE 32 trans-(3-Methyl-pyridin-2-yl)-{4-[2-(4-phenylpiperazin-1-yl)-ethyl]-cyclohexyl}-amine; mp 114–115° C.

EXAMPLE 33 trans-{4-[2-(4-Phenyl-piperazin-1-yl)-ethyl]-cyclohexyl}-pyridin-4-yl-amine; mp 185–187° C.

EXAMPLE 34 trans-{4-[2-(4-Phenyl-piperazin-1-yl)-ethyl]-cyclohexyl}-4-trifluoromethyl-pyrimidin-2yl)-amine
Step 1: Preparation of trans-(4-Tert-butoxycarbonylamino-cyclohexyl)-acetic acid 4-Nitrophenyl acetic acid (70 g, 0.386 mol) was treated in 1 liter of 0.35 M NaOH with 40 g Raney nickel catalyst at 3000 pounds per square inch (psi) of hydrogen pressure for 173 hours. The mixture was cooled, the catalyst was filtered, and the filtrate was concentrated to a volume of 600 mL and treated with 90 g (0.412 mol) di-tert-butyl dicarbonate in THF (1400 mL) for 16 hours at room temperature. THF was removed by concentration, and the pH was adjusted to 11 with 2N NaOH. Neutral material was extracted with $Et_2O$, and the aqueous phase was treated with potassium bisulfate ($KHSO_4$) to bring the pH to 4. A white precipitate formed and was filtered off, washed with water, and dried. Recrystallization from ethyl acetate yielded the pure trans-(4-tert-butoxycarbonylaminocyclohexyl)-acetic acid, 42 g (42%); mp 161–163° C.

Step 2: Preparation of trans-{4-[2-Oxo-2-(4-phenyl-piperazin-1-yl)-ethyl]-cyclohexyl}-carbamic acid tert-butyl ester To a colution containing trans-(4-tertbutoxycarbonylamino-cyclohexyl)-acetic acid (15.44 g, 0.06 mol), triethylamine (6.05 g, 0.06 mol) and 1-phenylpiperazine (9.73 g, 0.06 mol) in $CH_2Cl_2$ (250 mL) was added EDAC-HCl ((1-ethyl-(3dimethylaminopropyl)-carbodiimide hydrochloride (11.5 g, 0.06 mol)). The reaction mixture was stirred at room temperature 16 hours, then washed with water, 1N NaOH, brine, and dried ($MgSO_4$). The solvent was evaporated, and the residue was chromatographed on a flash silica gel column eluting with $CH_2Cl_2$ and then EtOAc. The product fractions were recrystallized from acetonitrile ($CH_3CN$) to yield 12.0 g (50%) of trans-{4-[2-oxo-2-(4-phenyl-piperazin-1-yl)-ethyl]-cylohexyl}-carbamic acid tert-butyl ester as white crystals; mp 197.5–200° C.

Step 3: Preparation of trans-{4-[2-oxo-2-(4-phenyl-piperazin-1-yl)-ethyl]-cylohexyl}-amine Trans-{4-[2-oxo-2-(4-phenyl-piperazin-1-yl)-ethyl]-cylohexyl}-carbamic acid tert-butyl ester (18.1 g, 0.045 mol) was taken up in MeOH (275 mL) and treated with 4 M HCl in dioxane (56 mL, 0.224 mol) and allowed to stand 22 hours. Concentration to dryness yielded a solid which was treated with 2N NaOH (175 mL) and extracted with $CH_2Cl_2$. The extracts were washed with water, brine, and dried ($Na_2SO_4$). After evaporation of the solvent, the residue was crystallized in $Et_2O$ yielding trans-{4-[2-oxo-2-(4-phenyl-piperazin-1-yl)-ethyl]-cylohexyl}-amine as a white solid, 11.2 g (83%); mp 90–93° C.

Step 4: Preparation of trans-N-{4-[2-(4-phenyl-piperazin-1-yl)-ethyl]-cyclohexylamine A suspension of $LiAlH_4$ (3.32 g, 0.0875 mol) in dry THF (125 mL) at 0° was treated with a solution of $AlCl_3$ (40 g, 0.03 mol) in dry $Et_2O$ (125 mL) and stirred for 30 minutes. Over a 10-minute period, a solution of trans-{4-[2-oxo-2-(4-phenyl-piperazin-1-yl)-ethyl]-cyclohexyl}-amine (10.54 g, 0.035 mol) in THF (150 mL) was added, and the reaction mixture was allowed to warm to room temperature. After 20 hours, the reaction mixture was cooled in ice-water and treated with THF (50 mL) containing $H_2O$ (3 mL), then with 50% NaOH (3 mL) and $H_2O$ (6 mL). The inorganic material was filtered off through a Celite pad, and the solids were washed thoroughly with THF. The combined filtrates were evaporated to dryness, and the residue was taken up in $CH_2Cl_2$, dried ($Na_2SO_4$), and concentrated to yield trans-N-{4-[2-(4-phenyl-piperazin-1-yl)-ethyl]-cyclohexylamine as a white solid, 9.64 g (96%), which was used without further purification; mp 65–70° C.

Step 5: Preparation of trans-{4-[2-(4-phenyl-piperazin-1-yl)-ethyl]-cyclohexyl}-4-trifluoromethyl-pyrimidin-2-yl)-amine A solution of 2-chloro-4-trifluoropyrimidine (0.44 g, 2.4 mmol), trans-N-{4-[2-(4-phenyl-piperazin-1-yl)-ethyl]-cyclohexylamine (0.576 g, 2.0 mmol) and triethylamine (1.45 g, 14.0 mmol) in absolute EtOH (100 mL) was heated under reflux 20 hours. The reaction mixture was evaporated to dryness, and the residue was taken up in $CH_2Cl_2$ and washed with 1 M $K_2CO_3$, brine, and dried ($Na_2SO_4$). The solvent was evaporated, and the residue was chromatographed on a flash silica gel column eluting with $CH_2Cl_2$ and then EtOAc. The product fractions were recrystallized from $Et_2O$-hexane to yield trans-{4-[2-(4-phenyl-piperazin-1-yl)-ethyl]-cyclohexyl}-4-trifluoromethyl-pyrimidin-2-yl)-amine 0.55 g (63%) white crystals; mp 164–165° C.

EXAMPLE 35 trans-(5-Methoxy-pyrimidin-2-yl)-{4-[2-(4-phenyl-piperazin-1-yl)-ethyl]-cylohexyl}-amine Step 1: Preparation of trans-N-{4-[2-(4-phenyl-piperazin-1-yl)-ethyl]-cyclohexyl}-N, N'-dicarbobenzyloxyguanidine A solution of trans-N-{4-[2-(4-phenyl-piperazin-1-yl)-ethyl]-cyclohexylamine (0.43 g, 1.5 mmol), S-methyl-N,N'-dicarbobenzyloxy isothiourea (Nowak K. and Kania L., *Rocz. Chem.*, 1969;43(11):1953–1960) (0.59 g, 1.65 mmol) and triethylamine (0.18 g, 1.8 mmol) in dimethylformamide (DMF) (50 mL) was stirred at room temperature 3 days. An additional amount of the starting amine (0.075 g, 0.26 mmol) was added, and the reaction mixture was allowed to stand one more day and then evaporated to dryness. The residue was recrystallized from $Et_2O$-hexane to yield trans-N-{4-[2-(4-phenyl-piperazin-1-yl)-ethyl]-cyclohexyl-N, N'-dicarbobenzyloxyguanidine 0.568 g (63%) white solid; mp 136–137° C.

Step 2: Preparation of trans-N-{4-[2-(4-phenyl-piperazin-1-yl)-ethyl]-cyclohexylguanidine Trans-N-{4-[2-(4-phenyl-piperazin-1-yl)-ethyl] cyclohexyl-N,N'-dicarbobenzyloxyguanidine (2.77 g, 4.63 mol) was hydrogenolyzed in MeOH (250 mL) under 48 psi hydrogen pressure in the presence of 20% palladium on carbon catalyst (0.25 g). Filtration of the reaction mixture, evaporation of the filtrate, and recrystallization of the residue from isopropanol (i-PrOH)-$Et_2O$ yielded 1.39 g (91%) of the product; mp 140–170° C.

Step 3: Preparation of trans-(5-Methoxy-pyrimidin-2-yl-{4-[2-(4-phenyl-piperazin-1-yl)-ethyl]-cyclohexyl}-amine A solution of 2-methoxy-3-(dimethylamino)-acrolein (Plumpe H. and Schegk E., *Archiv. der Pharmazie*, 1967;300:704–708) (0.452 g, 3.5 mmol), trans-N-{4-[2-4-phenyl-piperazin-1-yl)-ethyl]-cyclohexylguanidine (1.15 g, 3.5 mmol) and 1 M sodium methoxide (NaOMe) (7.5 mL) in MeOH (10 mL) was heated under reflux 20 hours. The mixture was cooled, the product filtered off, washed with $H_2O$, and recrystallized from $CH_3CN$ to yield a tan solid, 0.41 g (30%); mp 170–173° C.

In a process analogous to Example 35 using appropriate starting materials, the corresponding compounds of Formula I (Examples 36–38) are prepared as follows:

EXAMPLE 36 trans-(5-Methyl-pyrimidin-2-yl)-{4-[2-(4-phenyl-piperazin-1-yl)-ethyl]-cyclohexyl}-amine Prepared in 34% yield from commercially available 2-methyl-3-(dimethylamino)-acrolein; mp 190° C.

EXAMPLE 37 trans-(5-Phenyl-pyrimidin-2-yl-{4-[2-(4-phenyl-piperazin-1-yl)-ethyl]-cyclohexyl}-amine Prepared in 4% yield from phenylmalonaldehyde (Coppola G., Hardtmann G., and Huegi B., *J. Hetorocyclic Chem.*, 1974;11(1):51–56); mp 170° C.

EXAMPLE 38 trans-(4,6-Dimethyl-pyrimidin-2-yl-{4-[2-(4-phenyl-piperazin-1-yl)-ethyl]-cyclohexyl}-amine Prepared in 12% yield from 2,4-pentanedione; mp 127–129° C.

We claim:

1. A compound of Formula I

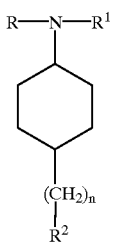

I wherein R is heteroaryl;
$R^1$ is hydrogen,
  lower alkyl,
  cycloalkyl,
  aryl, or
  benzyl;
n is an integer from 1 to 2;
$R^2$ is

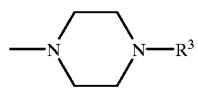

wherein $R^3$ is 2-pyrimidinyl,
  2-pyrimidinyl substituted by 1 to 2 substituents selected from the group consisting of
    lower alkyl,
    lower alkoxy, and
    halogen,
  2-quinazolinyl,
  4-quinazolinyl,
  2-, 3-, or 4-pyridinyl,
  2- or 3-thienyl,
  2-thiazolyl,
  2-pyrazinyl,
  phenyl, or
  phenyl substituted by 1 to 4 substituents selected from the group consisting of
    lower alkyl,
    lower alkoxy,
    hydroxy, halogen, and
    trifluoromethyl; and
the corresponding cis and trans isomers thereof; or a pharmaceutically acceptable acid addition salt thereof.

2. A compound according to claim 1, in which
R is 2-, 3-, or 4-pyridinyl,
  2-,3-, or 4-pyridinyl substituted by lower alkyl,
  2- or 4-pyrimidinyl,
  2- or 4-pyrimidinyl substituted by 1 to 2 substituents selected from lower alkyl, lower alkoxy, aryl, trifluoromethyl, or halogen,
  4-quinazolinyl,
  2-pyrazinyl,
  2-thiazolyl,
  2-benzothiazolyl,
  2-benzoimidazolyl, or
  2-benzoimidazolyl substituted by lower alkyl;
$R^1$ is hydrogen or methyl;
n is an integer of 2;
$R^2$ is

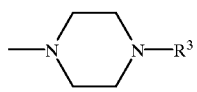

wherein $R^3$ is 2-pyrimidinyl,
  2-, 3-, or 4-pyridinyl,
  2- or 3-thienyl,
  2-thiazolyl,
  2-pyrazinyl,
  phenyl, or
  phenyl substituted by 1 to 4 substituents selected from the group consisting of lower alkyl,
    lower alkoxy,
    hydroxy, halogen, and
    trifluoromethyl.

3. A compound according to claim 2, in which
R is 2-, 3-, or 4-pyridinyl,
  2-(3-methyl-pyridinyl),
  2-, or 4-pyrimidinyl,
  2-(4-methyl-pyrimidinyl),
  2-(5-methyl-pyrimidinyl),
  2-(5-methoxy-pyrimidinyl),
  2-(5-phenyl-pyrimidinyl),
  2-(4-trifluoromethyl-pyrimidinyl),
  2-(5-fluoro-pyrimidinyl),
  2-(4,6-dimethyl-pyrimidinyl),
  4-quinazolinyl,
  2-pyrazinyl,
  2-thiazolyl,
  2-benzothiazolyl, or
  2-(1(N)-methyl-H-benzoimidazolyl;
$R^1$ is hydrogen or methyl;
n is an integer of 2;
$R^2$ is

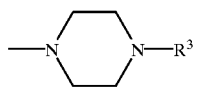

wherein $R^3$ is 2-pyrimidinyl,
  2-, 3-, or 4-pyridinyl,
  2- or 3-thienyl,
  2-thiazolyl,
  2-pyrazinyl,
  phenyl, or
  phenyl substituted by 1 to 2 substituents selected from the group consisting of lower alkyl,
lower alkoxy,
hydroxy, halogen, and
trifluoromethyl.

4. A compound according to claim 3 selected from the group consisting of:
cis-{4-[2-(4-Pyridin-2-yl-piperazin-1-yl)-ethyl]-cyclohexyl}-pyrimidin-2-yl-amine hydrochloride;
trans-{4-[2-(4-Pyridin-2-yl-piperazin-1-yl)-ethyl]-cyclohexyl}-pyrimidin-2-yl-amine;
trans-{4-[2-(4-Phenyl-piperazin-1-yl)-ethyl]-cyclohexyl}-pyrimidin-2-yl-amine;
trans-(4-{2-[4-(2,3-Dichloro-phenyl)-piperazin-1-yl]-ethyl}-cyclohexyl)-pyrimidin-2-yl-amine;
trans-(4-{2-[4-(2,3-Dichloro-phenyl)-piperazin-1-yl]-ethyl}-cyclohexyl)-methyl-pyrimidin-2-yl-amine;
trans-(4-{2-[4-(2,3-Dimethyl-phenyl)-piperazin-1-yl]-ethyl}-cyclohexyl)-pyrimidin-2-yl-amine;
trans-{4-[2-(4-Pyridin-2-yl-piperazin-1-yl)-ethyl]-cyclohexyl}-quinazolin-4-yl-amine;
trans-{4-[2-(4-Phenyl-piperazin-1-yl)-ethyl]-cyclohexyl}-quinazolin-4-yl-amine;
cis-{4-[2-(4-Phenyl-piperazin-1-yl)-ethyl]-cyclohexyl}-quinazolin-4-yl-amine;
cis-{4-[2-(4-Phenyl-piperazin-1-yl)-ethyl]-cyclohexyl}-pyrimidin-2-yl-amine hydrochloride;
trans-Methyl-{4-[2-(4-phenyl-piperazin-1-yl)-ethyl]-cyclohexyl}-pyrimidin-2-yl-amine;
trans-(5-Fluoro-pyrimidin-2-yl)-{4-[2-(4-phenyl-piperazin-1-yl)-ethyl]-cyclohexyl}-amine;
trans-Pyrimidin-2-yl-(4-{2-[4-(3-trifluoromethyl-phenyl)-piperazin-1-yl]-ethyl}-cyclohexy)-amine;
trans-(4-{2-[4-(2-Methoxy-phenyl)-piperazin-1-yl]-ethyl}-cyclohexyl)-pyrimidin-2-yl-amine;
trans-Pyrimidin-2-yl-{4-[2-(4-pyrimidin-2-yl-piperazin-1-yl)-ethyl]-cyclohexyl}-amine;
trans-(4-{2-[4-(4-Fluoro-phenyl)-piperazin 1-yl]-ethyl}-cyclohexyl)-pyrimidin-2-yl-amine;
trans-Pyrimidin-2-yl-{4-[2-(4-thiazol-2-yl-piperazin-1-yl)-ethyl]-cyclohexyl}-amine;
trans-(4-{2-[4-(4-Methoxy-phenyl)-piperazin1-yl]-ethyl}-cyclohexyl)-pyrimidin-2-yl-amine;
trans-Pyrimidin-2-yl-{4-[2-(2,3,5,6-tetrahydro-[1,2'] bipyrazinyl-4-yl)-ethyl]-cyclohexyl}-amine;
trans-{4-[2-(4-Pyridin-3-yl-piperazin-1-yl)-ethyl]-cyclohexyl}-pyrimidin-2-yl-amine;
trans-4-(4-{2-[4-(Pyrimidin-2-ylamino)cyclohexyl]-ethyl}-piperazin-1-yl)-phenol;
trans-{4-[2-(4-Phenyl-piperazin-1-yl)-ethyl]-cyclohexyl}-pyridin-3-yl-amine;
trans-{4-[2-(4-Phenyl-piperazin-1-yl)-ethyl]-cyclohexyl}-pyridin-2-yl-amine;
trans-(4-Methyl-pyrimidin-2-yl)-{4-[2-(4-phenyl-piperazin-1-yl)-ethyl]-cyclohexyl}-amine;
trans-{4-[2-(4-Phenyl-piperazin-1-yl)-ethyl]-cyclohexyl}-thiazol-2-yl-amine;
trans-{4-[2-(4-Phenyl-piperazin-1-yl)-ethyl]-cyclohexyl}-pyrazin-2-yl-amine;
trans-Benzothiazol-2-yl-{4-[2-(4-phenyl-piperazin-1-yl)-ethyl]-cyclohexyl}-amine;
cis-(1-Methyl-1H-benzoimidazol-2-yl)-{4-[2-(4-phenyl-piperazin-1-yl)-ethyl-}cyclohexyl}-amine;
trans-(1-Methyl-1H-benzomidazol-2-yl)-{4-[2-(4-phenyl-piperazin-1-yl)-ethyl]-cyclohexyl}-amine;
trans-{4-[2-(4-Phenyl-piperazin-1-yl)-ethyl]cyclohexyl}-pyrimidin-4-yl-amine;
trans-(3-Methyl-pyridin-2-yl)-{4-[2-(4-phenyl-piperazin-1-yl)-ethyl]-cyclohexyl}-amine;
trans-{4-[2-(4-Phenyl-piperazin-1-yl)-ethyl]cyclohexyl}-pyridin-4-yl-amine;
trans-{4-[2-(4-Phenyl-piperazin-1-yl)-ethyl]cyclohexyl}-4-trifluoromethyl-pyrimidin-2-yl)amine;
trans-(5-Methoxy-pyrimidin-2-1-yl)-{4-[2-(4-phenyl-piperazin-1-yl)-ethyl]-cylohexyl}-amine;
trans-(5-Methyl-pyrimidin-2-yl-{4-[2-(4-phenyl-piperazin-1-yl)-ethyl]-cyclohexyl}amine;
trans-(5-Phenyl-pyrimidin-2-yl-{4-[2-(4-phenyl-piperazin-1-yl)-ethyl]-cyclohexyl}amine; and
trans-(4,6-Dimethyl-pyrimidin-2-yl-{4-[2-(4phenyl-piperazin-1-yl)-ethyl]-cyclohexyl}amine.

5. A compound according to claim 4 which is trans-{4-[2-(4-Phenyl-piperazin-1-yl)-ethyl]-cyclohexyl}-pyrimidin-2-yl-amine.

6. A compound according to claim 1, in which R is 2-quinazolinyl, or 4-quinazolinyl.

7. A method of treating psychoses or anxiety comprising administering to a host suffering therefrom a therapeutic effective amount of a compound according to claim 1 in unit dosage form.

8. A method of treating schizophrenia comprising administering to a host suffering therefrom a therapeutic effective amount of a compound according to claim 1 in unit dosage form.

9. A pharmaceutical composition comprising a compound according to claim 1 in admixture with a pharmaceutically acceptable excipient, diluent, or carrier.

10. A method of preparing a compound having the Formula I

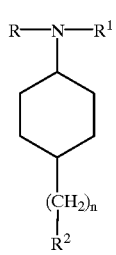

I wherein R is heteroaryl;
R¹ is hydrogen,
lower alkyl,
cycloalkyl,
aryl, or
benzyl;
n is an integer from 1 to 2;
R² is

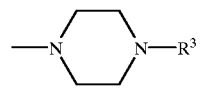

wherein R³ is 2-pyrimidinyl,
2-pyrimidinyl substituted by 1 to 2 substituents selected from the group consisting of lower alkyl, lower alkoxy, and halogen, 2-quinazolinyl, 4-quinazolinyl, 2-, 3-, or 4-pyridinyl, 2- or 3-thienyl, 2-thiazolyl, 2-pyrazinyl, phenyl, or phenyl substituted by 1 to 4 substituents selected from the group consisting of lower alkyl, lower alkoxy, hydroxy, halogen, and trifluoromethyl; and the corresponding cis and trans isomers thereof; or a pharmaceutically acceptable acid addition salt thereof comprises reacting a compound of Formula II

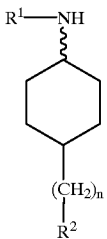

II wherein $R^1$, n, and $R^2$ are as defined above with a compound of Formula III

RX     III wherein X is Cl or Br and R is as defined above in the presence of a base and a solvent to give a compound of Formula I and optionally separating the mixture of cis and trans isomers of a compound of Formula I into the individual cis or trans isomer by conventional methodology and if desired, converting a compound of Formula I to a corresponding pharmaceutically acceptable acid addition salt by conventional means and, if so desired, converting the corresponding pharmaceutically acceptable acid addition salt to a compound of Formula I by conventional means.

* * * * *